United States Patent
Fong et al.

(10) Patent No.: US 6,423,539 B2
(45) Date of Patent: Jul. 23, 2002

(54) ADJUVANT TREATMENT BY IN VIVO ACTIVATION OF DENDRITIC CELLS

(75) Inventors: Lawrence H. Fong, Menlo Park; Miriam Merad, Palo Alto; Edgar G. Engleman, Atherton, all of CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/791,992

(22) Filed: Feb. 22, 2001

Related U.S. Application Data (60) Provisional application No. 60/184,810, filed on Feb. 24, 2000.

(51) Int. Cl.$^7$ .............................. C12N 5/00; C12N 5/06; C07K 1/00
(52) U.S. Cl. ....................... 435/325; 435/326; 435/339; 530/350; 530/351
(58) Field of Search ................................. 435/325, 326, 435/339; 530/350, 351

(56) References Cited

U.S. PATENT DOCUMENTS

| | | | |
|---|---|---|---|
| 5,976,546 A | 11/1999 | Laus et al. ................ | 424/152.1 |
| 5,994,126 A | 11/1999 | Steinman et al. ........... | 435/325 |

FOREIGN PATENT DOCUMENTS

| WO | WO 98/18923 | 5/1998 |
|---|---|---|

OTHER PUBLICATIONS

Hsu et al. (Jan. 1996), "Vaccination of Patients with B–Cell Lymphoma Using Autologous Antigen–Pulsed Dendritic Cells." *Nature Medicine,* vol. 2(1):52–58.
Maraskovsky et al. (Nov. 1996), "Dramatic Increase in the Numbers of Functionality Mature Dendritic Cells in Flt3 Ligand0Treated Mice: Multiple Dendritic Cell Subpopulations Identified." *J. Exp. Med.,* vol. 187:1953–1962.
Pulendran et al. (1997), "Deve;lopmental Pathways of Dendritic Cells in Vivo." *Journal of Immunology,* vol. 159:2222–2231.
Young et al. (Jan. 1996), "Dendritic Cells as Adjuvants for Class 1 Major Histocompatibility Complex–Restricted Antitumor Immunity." *J. Exp. Med.,* vol. 183:7–11.

*Primary Examiner*—Hankyel T. Park
(74) *Attorney, Agent, or Firm*—Pamela J. Sherwood; Bozicevic, Field & Francis LLP (57) ABSTRACT

The immunogenicity of an antigen is enhanced by increasing the specific antigen presenting function of dendritic cells (DC) in a mammalian host. The host is treated with a DC mobilization agent to increase the number of circulating DC precursors. The host is then given a local, injection of antigen in combination with a DC activating agent. The activation step promotes recruitment and maturation of the DC, along with antigen-specific activation and migration from the tissues to lymphoid organs. These DC then effectively interact with, and present processed antigen to, T cells that are then able to respond to the antigen. In one aspect of the invention, the antigen is a tumor antigen, and is used to enhance the host immune response to tumor cells present in the body.

19 Claims, 7 Drawing Sheets

A

| | %DC | Ratio mature/ Immature |
|---|---|---|
| CTR | 1.00% | |
| FL alone | 15% | 1 |
| FL+ ISS | 21% | 2 |
| FL+ ODN | 12% | 1 |

B

| | Mature DC | Immature DC |
|---|---|---|
| Class II | 400-476 | 28-33 |
| CD86 | 150-208 | 38-59 |
| CD40 | 35-44 | 20-25 |
| CD62 L | 191-212 | 68-89 |

|  | %DC | Ratio mature/ Immature |
|---|---|---|
| CTR | 1.00% |  |
| FL alone | 15% | 1 |
| FL+ ISS | 21% | 2 |
| FL+ ODN | 12% | 1 |

B

|  | Mature DC | Immature DC |
|---|---|---|
| Class II | 400-476 | 28-33 |
| CD86 | 150-208 | 38-59 |
| CD40 | 35-44 | 20-25 |
| CD62 L | 191-212 | 68-89 |

ADJUVANT TREATMENT BY IN VIVO ACTIVATION OF DENDRITIC CELLS

This application claims benefit to U.S. provisional application Serial No. 60/184,810, filed Feb. 24, 2000.

GOVERNMENT SUPPORT

This application was made with Government support under contract CA71725 awarded by the National Institutes of Health. The Government has certain rights in this invention.

While vaccination protocols have been some of the great medical achievements in the last century, there are still conditions where an effective immune response has been difficult to generate. For example, human tumor immunotherapy has met with only limited success. Among the reasons for this have been the limited availability of tumor-associated antigens, and an inability to deliver such antigens in a manner that renders them immunogenic. Recent insights into the role of dendritic cells (DC) as the pivotal antigen presenting cell for initiation of immune responses may provide the basis for more effective immune responses, particularly where conventional vaccination is inadequate.

The events whereby cells fragment antigens into peptides, and then present these peptides in association with products of the major histocompatibility complex, (MHC) are termed "antigen presentation". The MHC is a region of highly polymorphic genes whose products are expressed on the surfaces of a variety of cells. T cells recognize foreign antigens bound to only one specific class I or class II MHC molecule. The patterns of antigen association with class I or class II MHC molecules determine which T cells are stimulated.

T cells do not effectively respond to antigen unless the antigen is processed and presented to them by the appropriate antigen presenting cells (APC). The two major classes of antigen presenting cells are DC and macrophages. DC are uniquely capable of processing and presenting antigens to naive T cells. The efficacy of DC in antigen presentation is widely acknowledged, but the clinical use of these cells is hampered by the fact that there are very few in any given organ. In human blood, for example, about 1% of the white cells are DC. While DC can process foreign antigens into peptides that immunologically active T cells can recognize, the low numbers of DC makes their therapeutic use very difficult.

In recent years, the life cycle of DC has been elucidated. DC precursors migrate from bone marrow and circulate in the blood to specific sites in the body where they mature. This trafficking is directed by expression of chemokine receptors and adhesion molecules. Tissue resident DC include Langerhans cells in skin, hepatic DC in the portal triads, mucosal DC and lung DC. Upon exposure to antigen and activation signals, the DC are activated, and leave tissues to migrate via the afferent lymphatics to the T cell rich paracortex of the draining lymph nodes. The activated DC then secrete chemokines and cytokines involved in T cell homing and activation, and present processed antigen to T cells.

Mature DC have a distinct morphology characterized by the presence of numerous membrane processes. These processes can take the form of dendrites, pseudopods or veils. DC are also characterized by the cell surface expression of large amounts of class II MHC antigens and the absence of lineage markers, including CD14 (monocyte), CD3 (T cell), CD19, 20, 24 (B cell), CD56 (natural killer), and CD66b (granulocyte). DC express a variety of adhesion and co-stimulatory molecules, e.g. CD80 and CD86, and molecules that regulate co-stimulation, such as CD40. The phenotype of DC varies with the stage of maturation and activation, where expression of adhesion molecules, MHC antigens and co-stimulatory molecules increases with maturation. Antibodies that preferentially stain mature DC include anti-CD83 and CMRF-44.

While methods have been described for the in vitro manipulation of DC in order to enhance their immunologic function, such techniques can be very expensive and labor intensive. The ability to enhance DC antigen presentation in vivo (i.e. without in vitro culture) would be of great clinical and experimental benefit.

Relevant Literature

Administration of Flt3 ligand to mice in vivo results in preferential mobilization or release of DC precursors from the bone marrow to the periphery and into lymphoid organs, and can increase the number of circulating DC 10–30 fold (Maraskovsky et al. (1996) *J. Exp. Med.* 184:1953–1962). It has been suggested that these cells can then be removed for ex vivo manipulation and priming. Pulendran et al. (1997) *J. Immunol.* 159:2222–2231 describe the expansion of DC in animals treated with FL.

Hsu et al. (1996) *Nat. Med.* 2:52–58 describe vaccination of patients with B-cell lymphoma using autologous DC that had been removed from the patient, pulsed with antigen, and reinfused as an autologous vaccine. Young and Inaba (1996) *J. Exp. Med.* 183:7–11 describe the use of DC are adjuvants for class I MHC-restricted antitumor immunity.

U.S. Pat. No. 5,994,126, Steinman et a., issued Nov. 30, 1999 describes method for in vitro proliferation of DC precursors and their use to produce immunogens. U.S. Pat. No. 5,976,546, Laus et al., issued Nov. 2, 1999 describes immunostimulatory compositions.

SUMMARY OF THE INVENTION

Methods are provided for enhancing the immunogenicity of an antigen by increasing the specific antigen presenting function of DC in a mammalian host. Prior to the immunization with an antigen, the host is treated with a DC mobilization agent, e.g. Flt-3 ligand, GM-CSF, G-CSF/Flt3L fusion protein, etc. This treatment effectively increases the number of circulating DC precursors. The host is then given a local, e.g. sub-cutaneous, intramuscular, etc., injection of antigen in combination with a DC activating agent, e.g. immunostimulatory DNA sequences, IL-1, alpha interferon, LPS, endotoxin, CD40L, poly IC, etc. The activation step promotes recruitment and maturation of the DC, along with antigen-specific activation and migration from the tissues to lymphoid organs. These DC then effectively interact with, and present processed antigen to, T cells that are then able to respond to the antigen. The methods of the invention are particularly useful in situations where the host response to the antigen is sub-optimal, for example in conditions of chronic infection, a lack of immune response to tumor antigens, and the like. In one aspect of the invention, the antigen is a tumor antigen, and is used to enhance the host immune response to tumor cells present in the body.

DESCRIPTION OF THE SPECIFIC EMBODIMENTS

A two step protocol is provided for the enhancement of T cell mediated immune responses, in the absence of in vitro manipulation of DC. The initial step of the method provides for the expansion and mobilization in vivo of DC precursors, through administration of a DC mobilizing agent.

After the host has responded to the DC expansion and mobilization, usually from about 3 days to 2 weeks, there is an increased number of DC precursors in the peripheral tissues, e.g. skin, muscle, lungs, etc. These cells are not yet immunologically mature, but can respond to DC activating agents, which agents include a variety of immunostimulatory compounds. Of particular interest for this purpose are immunostimulatory polynucleotide sequences. The DC activating agent is preferably delivered directly to the peripheral tissues.

The antigen of interest is delivered to the peripheral tissues along with the DC activating agent, and may be given as a combined formulation, or as separate formulations. The antigen may be further provided in a booster dose, in combination with other adjuvants as known in the art, etc.

The activation and antigenic stimulation in the peripheral tissues activates the DC precursors to mature into functional DC, which are then able to take-up and process the antigen of interest. On maturation, the DC are competent to migrate to lymphatic organs, particularly T cell rich regions of the lymph nodes, where T cell activation occurs. Therefore, although the administration of antigen and activating agent is localized, the resulting immune response is not limited to that tissue.

Conditions of particular interest for use with the present methods involve a lack of T cell mediated response to antigen, for example chronic viral or bacterial infection, a lack of immune response to tumor antigens, and the like. In one aspect of the invention, the antigen is a tumor antigen, and is used to enhance the host immune response to tumor cells present in the body.

Mammalian species that may require enhancement of T cell mediated immune responses include canines and felines; equines; bovines; ovines; etc. and primates, particularly humans. Animal models, particularly small mammals, e.g. murine, lagomorpha, etc. may be used for experimental investigations. Animal models of interest include those involved with the immune response to infection and tumors.

Methods

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "an immunization" includes a plurality of such immunizations and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

DC mobilization agent, as used herein, refers to a compound, particularly a naturally occurring protein or derivative thereof, that acts on hematopoietic progenitor or stem cells to expand and mobilize precursors of DC. During mobilization, the DC precursors migrate from their tissue of origin, e.g. bone marrow, and move into the peripheral blood and peripheral tissues. Some mobilization agents will act broadly on the hematopoietic system, e.g. GM-CSF, etc. In a preferred embodiment, the mobilization agent will preferentially act to expand DC, e.g. by using Flt-3 ligand (FL) or a fusion molecule containing FL and at least one other growth or differentiation factor (e.g. G-CSF).

The dose of mobilizing agent will be effective to substantially increase the number of DC precursors in peripheral tissues. The increase in the number of DC precursors after the mobilization can be quite high, usually by at least about 2 fold, more usually by at least about 5 fold, and may be as high as a 20 or 75 fold increase. DC precursors mobilized by Flt3L typically express CD4, MHC class II, CD54, but lack expression of CD80, and may be identified by these criteria.

The term "dendritic cell" refers to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells).

The length of time required for expansion and mobilization is usually at least about 3 or 4 days, more usually at least about 1 week, and can take about 10 days to 2 weeks for optimal expansion. The length of time allotted for mobilization and expansion can be predicted based on previous trials with the mobilizing agent at a similar dose, or may be monitored individually by quantitating the change in the number of DC precursors present in the peripheral blood.

Various routes and regimens for delivery of the mobilization agent may be used, as known and practiced in the art. For example, where the mobilization agent is FL, the FL may be administered daily, where the dose is from about 1 to 100 mg/kg body weight, more usually from about 10 to about 50 mg/kg body weight, up to a maximum dose of about 1 to 2 mg daily. Administration may be at a localized site, e.g. sub-cutaneous, or systemic, e.g. intraperitoneal, intravenous, etc.

Flt3 or Flk2 is a tyrosine kinase receptor structurally related to macrophage colony-stimulating factor (CSF1) and to mast cell growth factor receptor (c-kit). The FL is a growth factor that stimulates the proliferation of certain hematopoietic progenitor cells. FL mRNA is widely expressed in human tissues. The genetic sequence of murine and human FL is described by Lyman et al. (1993) *Cell* 75: 1157–1167; and Lyman et al. (1994) *Blood* 83: 2795–2801 (Genbank accession numbers L23636, and U03858, respectively).

For use in the subject methods, a native FL or modifications thereof may be used. The FL sequence may be from any mammalian or avian species, e.g. primate sp., particularly humans; rodents, including mice, rats and hamsters;

rabbits; equines, bovines, canines, felines; etc. Of particular interest is the human protein. Generally, for in vivo use the FL sequence will have the same species of origin as the animal host.

The nucleic acid sequences encoding the human FL polypeptides may be accessed from public databases as previously cited. Identification of non-human Flt-3 ligands is accomplished by conventional screening methods of DNA libraries or biological samples for DNA sequences having a high degree of similarity to known Flt-3 ligand sequences.

The sequence of the FL polypeptide may be altered in various ways known in the art to generate targeted changes in sequence. The polypeptide will usually be substantially similar to the sequences provided herein, i.e. may differ by one more amino acids, but not usually more than about ten amino acids. The sequence changes may be substitutions, insertions or deletions. Scanning mutations that systematically introduce alanine, or other residues, may be used to determine key amino acids. Deletions may further include larger changes, such as deletions of a domain or exon, providing for active peptide fragments of the protein. Other modifications of interest include epitope tagging, e.g. with the FLAG system, HA, etc. Such alterations may be used to alter properties of the protein, by affecting the stability, specificity, etc.

The protein may be joined to a wide variety of other oligopeptides or proteins for a variety of purposes. By providing for expression of the subject peptides, various post-expression modifications may be achieved.

The FL for use in the subject methods may be produced from eukaryotic or prokaryotic cells. Where the protein is produced by prokaryotic cells, it may be further processed by unfolding, e.g. heat denaturation, DTT reduction, etc. and may be further refolded, using methods known in the art.

DC activating agent. Following the expansion and mobilization step, the host periphery will have increased numbers of DC precursors. These cells are not highly active antigen presenting cells, but can be induced to mature into APC. The maturation process is stimulated by a combination of DC activating agent, and the antigen of interest.

The presence of DC precursors in the periphery indicates that that the most effective route for delivering the activating agent is through a local delivery, particularly dermal, subcutaneous and intramuscular administration (see U.S. Pat. No. 5,830,877, Carson et al., issued Nov. 3, 1998). Generally the antigen and the DC activating agent will be delivered to the same site, and may be co-formulated, e.g. mixed together, coadministered, conjugated together, etc.; or formulated separately, depending on the requirements of the specific agents.

A number of DC activating agents are known in the art, including LPS and endotoxins in small doses, alpha interferons, interleukin-1 (see Boraschi et al. (1999) *Methods* 19(1):108–13), modified tumor necrosis factor, CD40 ligand, poly IC, etc. Of particular interest is the use of immunostimulatory polynucleotide sequences (ISS), which have been shown to be highly effective in the activation of DC, and other antigen presenting cells. The use of these sequences is known in the art, for examples see Bauer et al. (1999) *Immunology* 97(4):699–705; Klinman et al (1999) *Vaccine* 17(1):19–25; Hasan et al. (1999) *J Immunol Methods* 229(1–2):1–22; and others.

An "immunostimulatory oligonucleotide" refers to an oligonucleotide that contains a cytosine/guanine dinucleotide sequence and stimulates maturation and activation of DC. An immunostimulatory oligonucleotide of interest may be between 2 to 100 base pairs in size and typically contain a consensus mitogenic CpG motif represented by the formula: 5'$X_1X_2CGX_3X_4$3', where C and G are unmethylated, $X_1$, $X_2$, $X_3$ and $X_4$ are nucleotides and a GCG trinucleotide sequence is not present at or near the 5' and 3' termini (see U.S. Pat. No. 6,008,200, Krieg et al., issued Dec. 28, 1999, herein incorporated by reference).

Preferably the immunostimulatory oligonucleotides range between 8 to 40 base pairs in size. In addition, the immunostimulatory oligonucleotides are preferably stabilized oligonucleotides, particularly preferred are phosphorothioate stabilized oligonucleotides. In one embodiment, $X_1 X_2$ is the dinucleotide GpA. In another embodiment, $X_3 X_4$ is the dinucleotide TpC or TpT.

The dose and protocol for delivery of the DC activating agent will vary with the specific agent that is selected. Typically one or more doses are administered. One particular advantage of the use of ISS in the methods of the invention is that ISS exert immunomodulatory activity even at relatively low dosages. Although the dosage used will vary depending on the clinical goals to be achieved, a suitable dosage range is one which provides from about 1 Fg to about 1,000 Fg or about 10,000 Fg of ISS in a single dosage. Alternatively, a target dosage of ISS can be considered to be about 1–10 FM in a sample of host blood drawn within the first 24–48 hours after administration of ISS. Based on current studies, ISS are believed to have little or no toxicity at these dosage levels.

Concurrent with the administration of a DC activating agent, antigen is provided in one or more doses. Preferably the initial dose of antigen is given at the same site as the DC activating agent. Subsequent doses may be given at the same or a different site, and may utilize other adjuvants as desired.

Antigens of interest include polypeptides and other immunogenic biomolecules, which may be isolated or derived from natural sources, produced by recombinant methods, etc., as known in the art. Alternatively complex antigens may be used, for example cell lysates, virus which may be inactivated, bacterial cells or fractions derived therefrom, and the like.

The formulations are useful when used in conjunction with vaccines such as, but not limited to, those for treating chronic bacterial infections, e.g. tuberculosis, etc.; chronic viral infections such as those associated with herpesvirus, lentivirus and retrovirus, etc. Antigens of interest may also include allergens, e.g. for the conversion of a Th2 to a Th1 type response. The antigens which may be incorporated into the present formulations include viral, prokaryotic and eukaryotic antigens, including but not limited to antigens derived from bacteria, fungi, protozoans, parasites and tumor cells.

Potential tumor antigens for immunotherapy include tumor specific antigens, e.g. immunoglobulin idiotypes and T cell antigen receptors; oncogenes, such as p21/ras, p53, p210/bcr-abl fusion product; etc.; developmental antigens, e.g. MART-1/Melan A; MAGE-1, MAGE-3; GAGE family; telomerase; etc.; viral antigens, e.g. human papilloma virus, Epstein Barr virus, etc.; tissue specific self-antigens, e.g. tyrosinase; gp100; prostatic acid phosphatase, prostate specific antigen, prostate specific membrane antigen; thyroglobulin, α-fetoprotein; etc.; and over-expressed self antigens, e.g. her-2/neu; carcinoembryonic antigen, muc-1, and the like.

Tumor cell derived protein extracts or RNA may be used as a source of antigen, in order to provide multiple antigens and increase the probability of inducing immunity to more than one tumor associated antigen. Although the target antigens are initially undefined, the immunogen can be later identified.

As an alternative to injecting antigen along with the DC activating agent, endogenous tissues expressing antigen can be used as an endogenous source of antigen. For example, tumors that express a tumor antigen maybe injected with the DC activating agent in conjunction with DC expansion to serve as the source to tumor antigen. The DC activating agent would serve to recruit and activated DC within the tumor where they would be capable of taking up tumor derived antigen.

A number of antigens expressed on normal tissues as well as tumors are useful as immunotherapy targets, and have been shown to stimulate T cell responses when the antigens are presented by DC.

Antigenic formulations will typically contain from about 0.1 $\mu$g to 1000 $\mu$g, more preferably 1 $\mu$g to 100 $\mu$g, of the selected antigen. The antigen composition may additionally contain biological buffers, excipients, preservatives, and the like.

The antigen is administered to the host in the manner conventional for the particular immunogen, generally as a single unit dose of an antigen in buffered saline, combined with the adjuvant formulation, where booster doses, typically one to several weeks later, may additionally be delivered enterally or parenterally, e.g., subcutaneously, intramuscularly, intradermally, intravenously, intraarterially, intraperitoneally, intranasally, orally, etc. Subcutaneous or intramuscular injection is, however, preferred.

EXPERIMENTAL

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

Example 1

Figure 1:
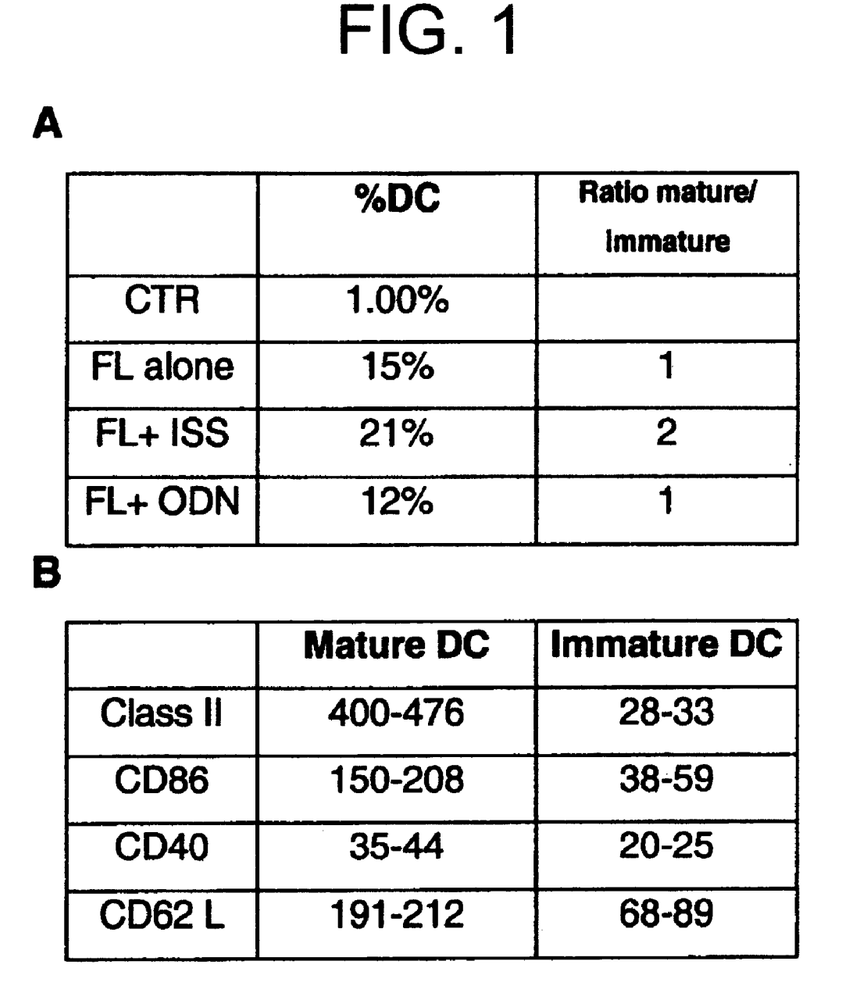
FIG. 1. ISS activate FL mobilized DC in vivo.

In animal studies, it was found that immunostimulatory nucleic acid sequences were are to activate dendritic cell precursors that had been mobilized in vivo. The results are shown in FIG. 1. Mice received 9 days of FL followed by 1 s.c injection of ISS, ODN or PBS 4 days later DC were collected from the LN and analyzed by flow cytometry. (A) DC were defined as MHC class II positive and CD11c positive cells. Mature DC are distinguished from immature DC by their high surface expression levels of MHC class II, CD86, CD40, and CD62L. The ratio of mature vs. immature DC were calculated for each group of mice. (B) The mean channel fluorescence range of mature vs. immature DC is demonstrated.

Figure 2:
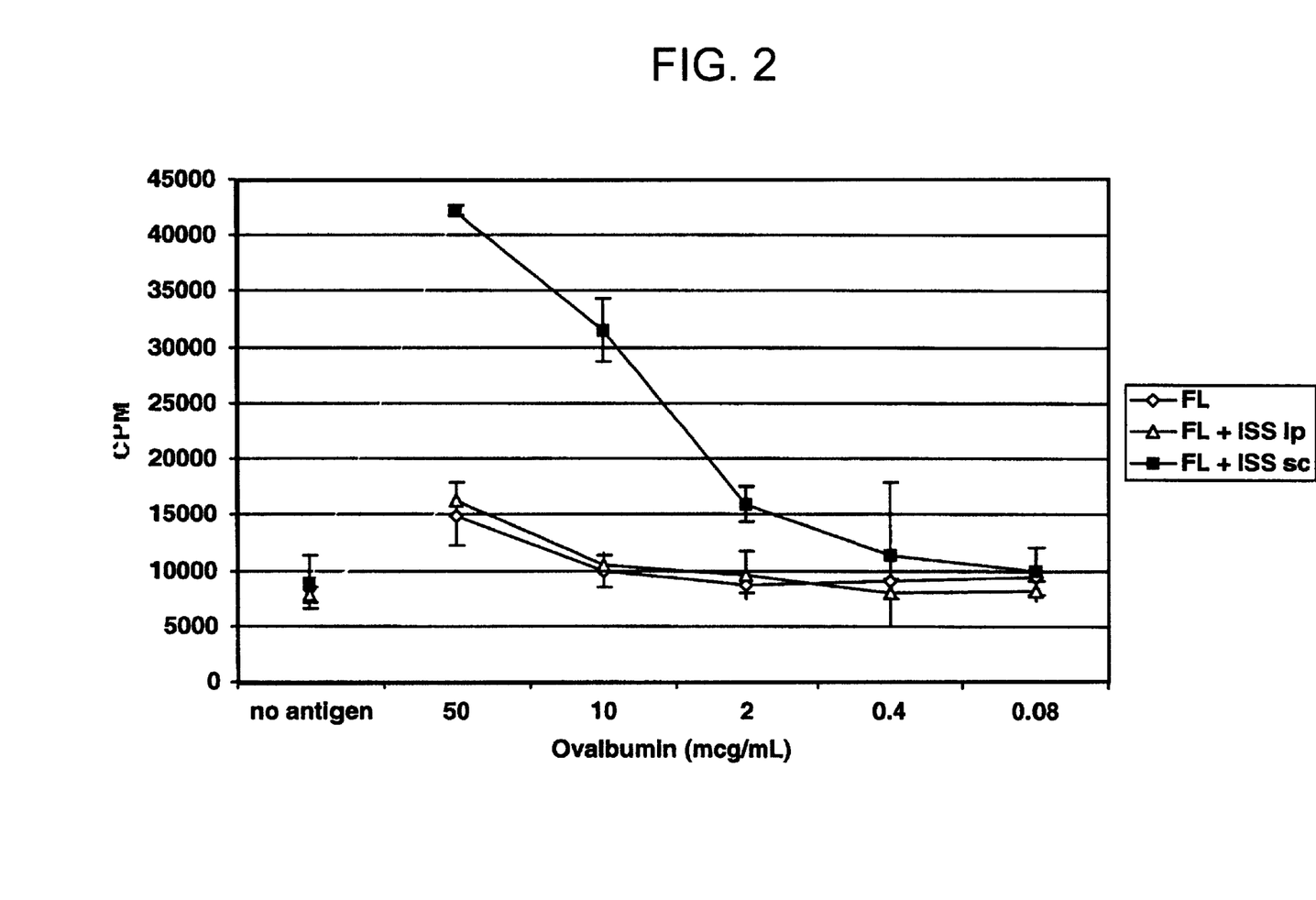
FIG. 2. ISS increase the immunogenicity of FL mobilized DC in vivo.

The treatment also increased the immunogenicity of FL mobilized DC in vivo. In order to analyze the immunogenicity induced by the association of ISS and FL, FL treated mice were injected s.c. with ISS, ODN or PBS mixed with ovalbumin into the foot pad. The draining LN were collected 1 week later and T cells were tested for their ability to proliferate in presence of antigen. As shown in FIG. 2, ISS dramatically increases T cell priming.

Figure 3:
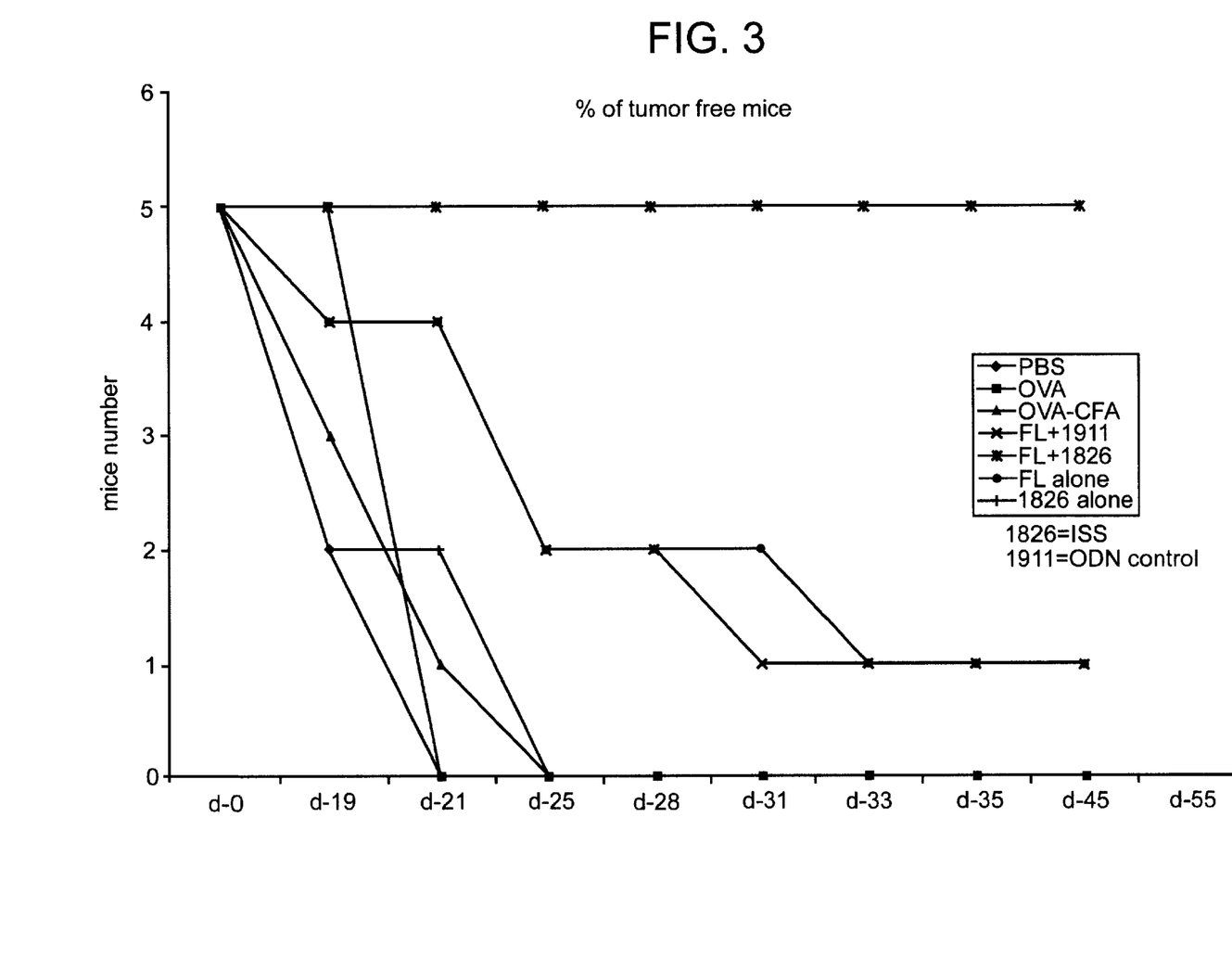
FIG. 3. Studies of the antitumor effect of a treatment combining FL and ISS.

To determine whether the combined treatment of FL+ISS would be able to vaccinate against syngeneic tumors, mice were injected ip with FL for 10 day period. Groups of mice received FL alone or 1 s.c. injection of ISS or ODN in association with FL. All the groups were immunized with ovalbumin. One week later the mice were injected s.c. with tumor cells from B16 melanoma transduced with ovalbumin gene. The group treated with FL+ISS did not develop any tumors while the other groups developed tumors at different time points. The ISS dramatically increased the antitumor effect of FL, and ODN did not induce any antitumor response. 6 weeks after the first immunization the mice were challenged with the same tumor cells. Only one out of 5 mice treated with FL+ISS developed small tumors, while the other 4 mice did not develop any tumors and survived greater than 60 days after follow-up. The data is shown in FIG. 3.

Figure 4:
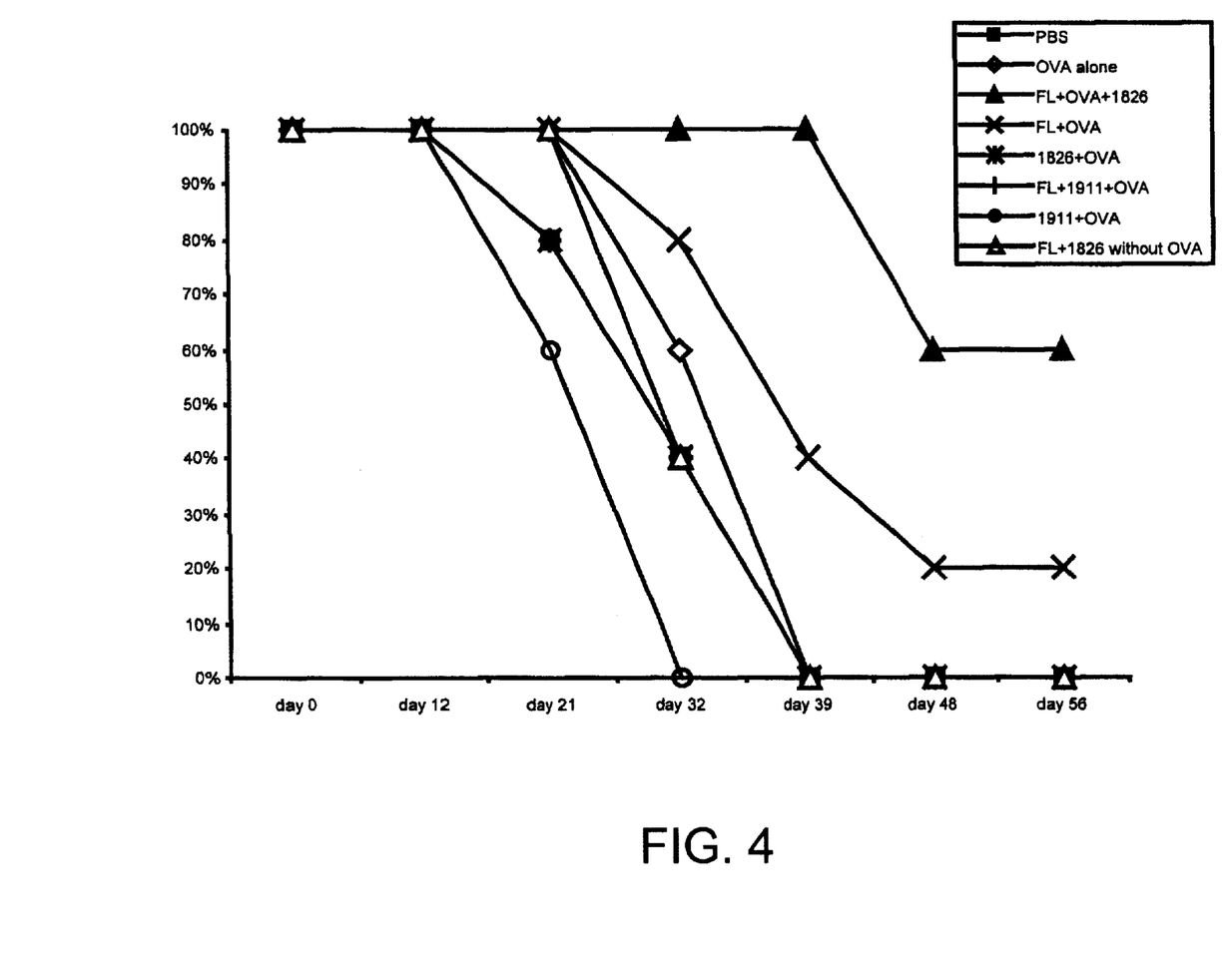
FIG. 4. Treatment of preexisting tumors with the combination of FL and ISS.

Preexisting tumors could also be treated with the combination of FL and ISS. To determine whether combined treatment of FL+ISS would be able to vaccinate animals bearing tumor, mice were initially injected s.c. with B16 melanoma transduced with ovalbumin gene. 5 days later, mice started on 10 daily injections of FL ip. On the final day of FL treatment, mice were immunized with ovalbumin with or without ISS. By six weeks following tumor challenge, all control mice had developed tumors, while only 40% of the mice in the FL+ISS group developed tumors, shown in FIG. 4.

Clinical studies were also performed to determine the effect of the activation methods in human patients. It was shown that administration of FL to patients with advanced cancer mobilizes DC precursors into the blood, resulting in an increase of circulating DC of 20 fold on average.

Figure 5:
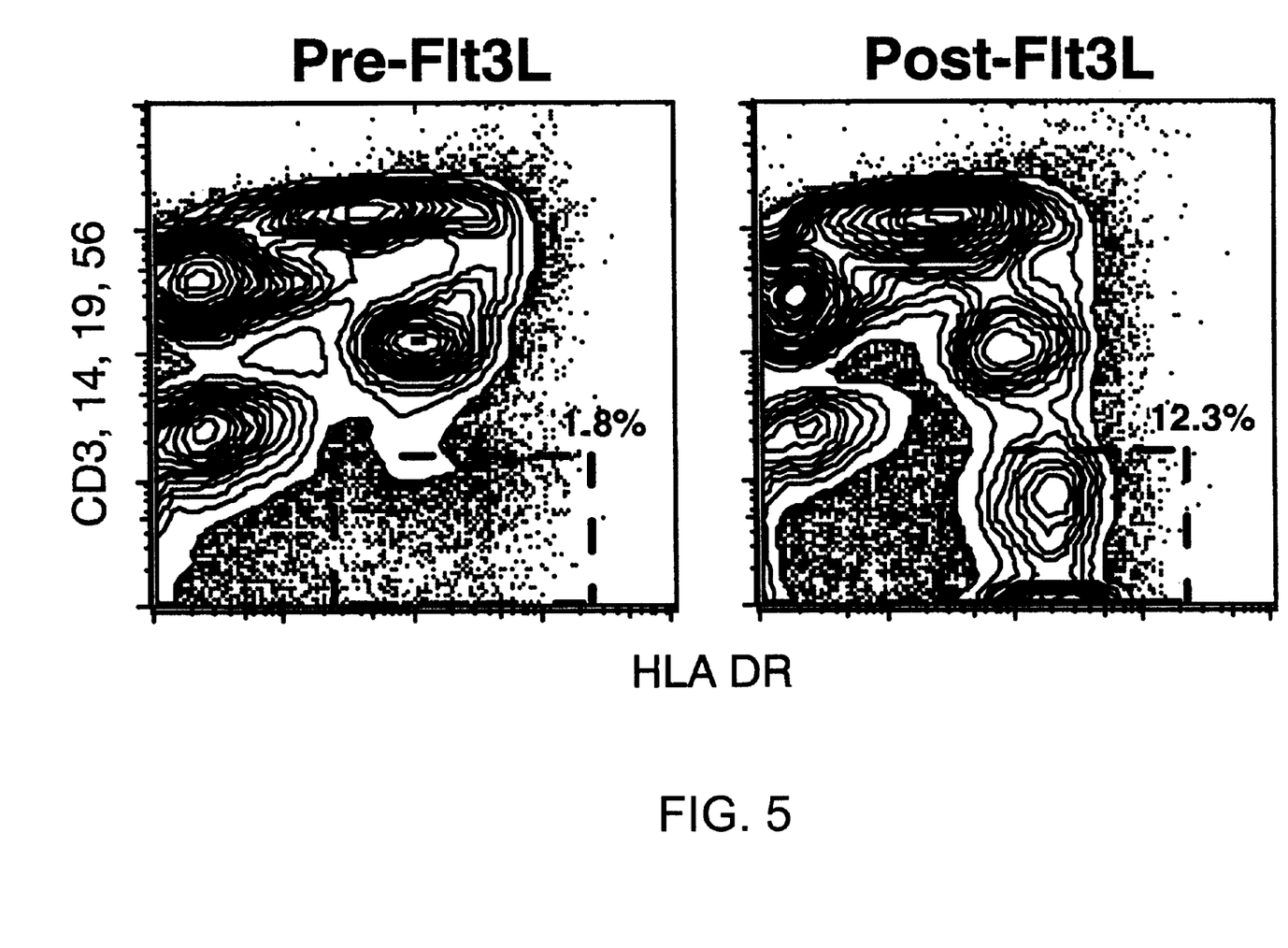
FIG. 5. Expansion of circulating blood DC following Flt3L administration.

An expansion of circulating blood DC was found following Flt3L administration. PBMC from patients with advanced cancer were assessed either before or following 10 days of Flt3L administration. DC were characterized phenotypically by expression of HLA DR without expression of lineage markers (CD3, 14, 19, 56). Patients developed a significant increase in circulating blood DC precursors as assessed by flow cytometry, shown in FIG. 5.

Figure 6:
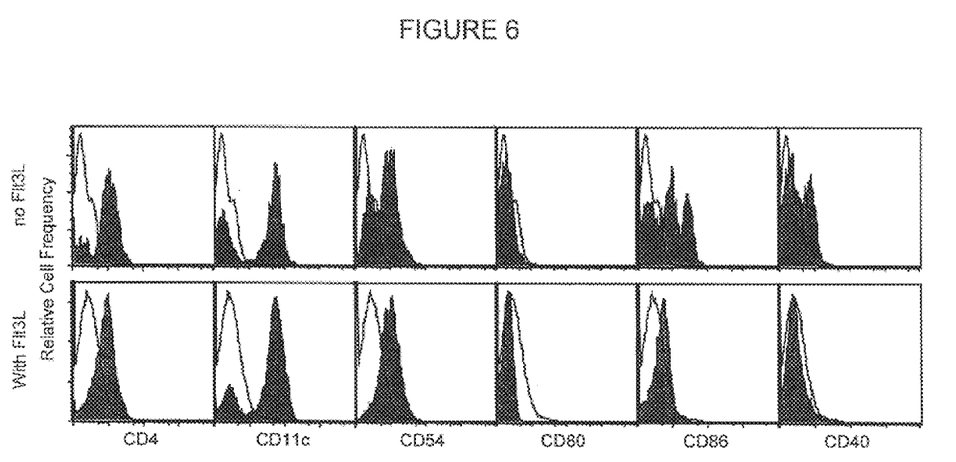
FIG. 6. Flt3L expanded human DC possess an immature phenotype.

The Flt3L expanded human DC possessed an immature phenotype, shown in FIG. 6. DC were gated on their expression of HLA DR and lack of lineage markers CD3, 14, 19, 56. Flt3L expanded DC express intermediate levels of CD4 and CD54 more homogeneously by comparison with unmobilized DC. Flt3L expanded DC, however, lack surface expression of CD86 and CD40 compared with unmobilized DC. Results are from one patient and are representative of three patients studied.

Figure 7:
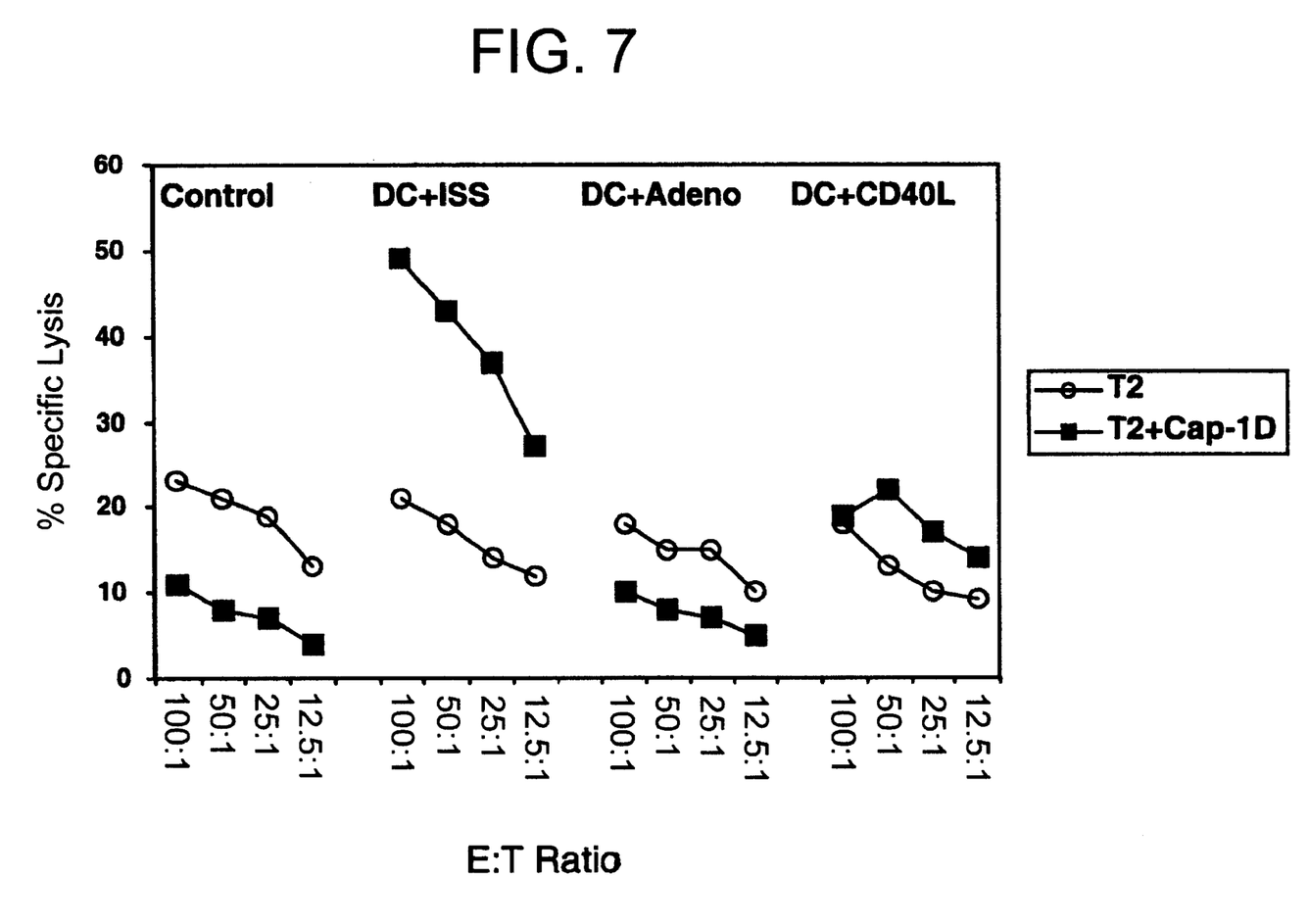
FIG. 7. In vitro induction of CTL with human DC mobilized with FL in vivo.

These in vivo mobilized cells were shown to be capable of inducing CTL in vitro. To assess the ability of FL mobilized DC to prime CD8 cytotoxic T lymphocytes (CTL) in vitro, DC precursors were purified with immunomagnetic beads following FL mobilization in vivo. Purified DC were then cultured overnight with the target peptide Cap-1D alone or in the presence of activating agents ISS, adenovirus (Adeno), or CD40L. Purified DC were then irradiated and cultured with purified autologous CD8 T cells. Subsequent CTL cultures where then assess by 4 hour $^{51}$Cr release assay for their ability to kill target cell line T2 with or without the target peptide Cap-1D. Induction of antigen specific CTL were only seen in CTL cultures using ISS activated DC as the stimulating antigen presenting cell, shown in FIG. 7.

It is apparent from the above results that an effective stimulation of immune response can be gained by mobilizing dendritic cell precursors, following by activation and antigenic stimulation. The methods result in a tumor specific immune response against new, and pre-existing tumors.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of increasing the immune response in a mammalian host to a target antigen in the absence of in vitro manipulation of dendritic cells, the method comprising:

administering to said mammalian host a dose of a DC mobilization agent effective to substantially increase the number of DC precursors present in the periphery of said host;

administering to said mammalian host a dose of a DC activation agent effective to induce maturation of said DC precursors in combination with said target antigen;

wherein the immune response of said mammalian host to said antigen is increased.

2. The method of claim 1, wherein said DC mobilization agent is Flt-3 ligand.

3. The method of claim 2, wherein said dose is effective in increasing the number of DC precursors in the periphery by at least 2 fold.

4. The method of claim 3, wherein said increased number of DC precursors is seen after one week.

5. The method of claim 1, wherein said DC activating agent is administered after the number of DC precursors has increased at least about 5 fold.

6. The method of claim 1, wherein said DC activating agent is an immunostimulatory polynucleotide.

7. The method of claim 1, wherein said DC activating agent is administered at a peripheral site.

8. The method of claim 7, wherein said administration is sub-cutaneous.

9. The method of claim 8, wherein said antigen and said DC activating agent are co-formulated.

10. The method of claim 8, wherein said antigen and said DC activating agent are separately formulated.

11. The method of claim 1, wherein said target antigen is a tumor antigen.

12. The method of claim 1, wherein said target antigen is a bacterial antigen.

13. The method of claim 1, wherein said target antigen is a viral antigen.

14. The method of claim 1, wherein said target antigen is in the form of peptides, protein, or nucleic acids encoding peptides or proteins.

15. The method of claim 1, wherein said mammalian host is a human.

16. A method of increasing a T cell mediated immune response in a mammalian host to a target antigen in the absence of in vitro manipulation of dendritic cells, the method comprising:

administering to said mammalian host a dose of Flt-3 ligand effective to substantially increase the number of DC precursors present in the periphery of said host; and after the number of DC precursors has increased at least about 5 fold in response to Flt-3 ligand, administering subcutaneously to said mammalian host a dose of a DC activation agent effective to induce maturation of said DC precursors in combination with said target antigen;

wherein the immune response of said mammalian host to said antigen is increased.

17. The method of claim 16, wherein said DC activating agent is an immunostimulatory polynucleotide.

18. The method of claim 17, wherein said target antigen is a tumor antigen.

19. The method of claim 16, wherein said mammalian host is a human.

* * * * *